United States Patent [19]

Gerke

[11] Patent Number: 5,470,989
[45] Date of Patent: Nov. 28, 1995

[54] PROCESS FOR THE PRODUCTION OF MIXTURES OF STEREOISOMERS OF 8,12-OXIDO-13,14,15,16-TETRANORLABDANE

[75] Inventor: Thomas Gerke, Neuss, Germany

[73] Assignee: Henkel Kommanditgesellschaft auf Aktien, Duesseldorf, Germany

[21] Appl. No.: 186,000

[22] PCT Filed: Jul. 10, 1992

[86] PCT No.: PCT/EP92/01565

§ 371 Date: Jan. 18, 1994

§ 102(e) Date: Jan. 18, 1994

[87] PCT Pub. No.: WO93/02073

PCT Pub. Date: Feb. 4, 1993

[30] Foreign Application Priority Data

Jul. 18, 1991 [DE] Germany .......................... 41 23 767.6

[51] Int. Cl.⁶ .................................................. C07D 307/92
[52] U.S. Cl. .............................................................. 549/458
[58] Field of Search ............................................... 549/458

[56] References Cited

U.S. PATENT DOCUMENTS

| 3,050,532 | 8/1962 | Schumacher et al. | 260/343.3 |
| 4,503,240 | 3/1985 | Staiger et al. | 549/458 |
| 5,274,134 | 12/1993 | Bruns et al. | 549/458 |

FOREIGN PATENT DOCUMENTS

| 3240054 | 5/1984 | Germany . |
| 3912318 | 10/1990 | Germany . |
| 9012793 | 11/1990 | WIPO . |

*Primary Examiner*—Bernard Dentz
*Attorney, Agent, or Firm*—Wayne C. Jaeschke; Norvell E. Wisdom, Jr.; Henry E. Millson, Jr.

[57] ABSTRACT

Stereoisomer mixtures of 8,12-oxido-13,14,15,16-tetranorlabdane are obtained in yields of at least 95% by dehydrating cyclization of stereoisomer mixtures of 8,12-dihydroxy-13,14,15,16-tetranorlabdane in the presence of acid-loaded aluminum oxide.

19 Claims, No Drawings

PROCESS FOR THE PRODUCTION OF MIXTURES OF STEREOISOMERS OF 8,12-OXIDO-13,14,15,16-TETRANORLABDANE

This application is a 371 of PCT/EP92/01565 filed on Jul. 10, 1992.

FIELD OF THE INVENTION

This invention relates to a process for the production of stereoisomer mixtures of 8,12-oxido-13,14,15,16-tetranorlabdane by cyclizing dehydration of 8,12-dihydroxy- 13,14,15,16-tetranorlabdane in the presence of acid-loaded aluminum oxide.

STATEMENT OF RELATED ART $8\alpha,12$-oxido-13,14,15,16-tetranorlabdane, hereinafter referred to as AMBROXAN®, is a much sought-after fragrance with a pronounced odor of ambergris. Synthetically, AMBROXAN® can be obtained from sclareol in a multistep synthesis sequence. For example, the odorless diol, $8\alpha,12$-dihydroxy-13,14,15,16-tetranorlabdane, can be prepared by oxidative side-chain degradation of sclareol in accordance with U.S. Pat. No. 3,050,532 and subsequent reduction of the lactone formed. Dehydrating cyclization of this diol gives AMBROXAN®. Numerous acidic catalysts have been described in the literature for this cyclization. Particular emphasis is placed in this regard on DE 39 12 318 A1 which describes a process for the stereoselective preparation of AMBROXANE® using acid-loaded aluminum oxide.

STATEMENT OF RELATED ART

However, the preparation of stereoisomers of $8\alpha,12$-oxido-13,14,15,16-tetranorlabdane is not readily possible without losses of yield. Thus, P. F. Vlad and N. D. Ungur have investigated the preparation of the 8-epi and 9-epi isomers with that of AMBROXAN® by ring closure of the corresponding 1,4-diol intermediates with dimethyl sulfoxide/trimethyl chlorosilane. They found that the cyclization yield is dependent to a large extent on the stereochemistry of the product. Whereas $8\alpha,12$-oxido-13,14,15,16-tetranorlabdane and its 9-epi isomer were obtained in yields of 85% and 90%, respectively, the 8-epi isomer was obtained in a yield of only 46%.

It is also known that mixtures of stereoisomers of $8\alpha,12$-oxido-13,14,15,16-tetranorlabdane have a pronounced ambergris odor. Thus, DE 32 40 054 A1 describes a process for the preparation of a mixture of stereoisomers of $8\alpha,12$-oxido-13,14,15,16-tetranorlabdane. In this process, homofarnesylic acid is cyclized to norambreolide in the presence of titanium tetrachloride and/or certain tin compounds, the norambreolide is then converted into a 1,4-diol and the 1,4-diol is cyclized to 8,12-oxido-13,14,15,16-tetranorlabdane. According to the Example of DE 32 40 054 A1, the yield of the last-mentioned cyclization is only 65%.

DESCRIPTION OF THE INVENTION

Object of the Invention

Accordingly, the problem addressed by the present invention was to provide a process in which stereoisomer mixtures of 8,12-dihydroxy-13,14,15,16-tetranorlabdane could be converted in high yields into a stereoisomer mixture of 8,12-oxido-13, 14,15,16-tetranorlabdane.

SUMMARY OF THE INVENTION

It has now surprisingly been found that stereoisomer mixtures of 8,12-dihydroxy- 13,14,15,16-tetranorlabdane can be converted into stereoisomer mixtures of 8,12-oxido-13,14,15,16-tetranorlabdane in yields of at least 95% if the cyclization is carried out in the presence of acid-loaded aluminum oxide.

Accordingly, the present invention relates to a process for the production of stereoisomer mixtures of 8,12-oxido-13,14,15,16-tetranorlabdane by cyclizing dehydration of stereoisomer mixtures of 8,12-dihydroxy-13,14,15,16-tetranorlabdane with acid-loaded aluminum oxide.

DESCRIPTION OF PREFERRED EMBODIMENTS

The process according to the invention is carried out at temperatures of 120° to 180° C. and preferably at temperatures of 140° to 160° C. The cyclization may be carried out in the absence of solvents, but is preferably carried out in inert solvents, for example toluene, xylene or methyl cyclohexane. Small quantities of water adsorbed onto the acid-loaded aluminum oxide and also the water formed during the cyclization can readily be removed by azeotropic distillation.

The acid-loaded aluminum oxide is used in a quantity of 40 to 100% by weight and preferably in a quantity of 60 to 80% by weight, based on the 8,12-dihydroxy- 13,14,15,16-tetranorlabdane.

Acids suitable for loading the aluminum oxide can be determined in a simple test: The pH value of a 5% by weight aqueous dispersion of aluminum oxide with an acid adsorbed onto its surface is measured. If this pH value is between 3 and 5.5, the corresponding acid is suitable for the loading of aluminum oxide. Acids in which a pH value of 4 to 5 is found in this test are preferably used. The mineral acids hydrochloric acid, sulfuric acid, nitric acid and phosphoric acid and the hydrohalic acids hydrofluoric acid, hydrochloric acid, hydrobromic acid and hydriodic acid are particularly suitable.

The aluminum oxide is preferably used in granular form, particle sizes of 0.05 to 0.2 mm (70 to 290 mesh) being particularly suitable.

Stereoisomer mixtures of 8,12-dihydroxy-13,14,15,16-tetranorlabdane are known from the literature, for example from DE 32 40 054 A1. According to the invention, however, any other stereoisomer mixtures of 8,12-dihydroxy-13,14,15,16-tetranorlabdane may also be used for the cyclization. The stereoisomer mixtures used may also contain secondary products formed during their preparation. For example, the diols obtained in accordance with DE 32 40 054 A1 (Example 1 a–d) are complex mixtures of stereoisomeric alcohols of which some could not be fully identified. Mixtures such as these may also contain fractions from the preceding reaction stages. For example, olefinic protons indicative of acyclic structures were detected by NMR spectroscopy. The secondary products present in the diol mixtures do not adversely affect the odor of the AMBROXAN® produced by the process according to the invention. If desired, the diol mixtures used may be purified by distillation to remove secondary products. The odor intensity of the AMBROXAN® produced in accordance with the invention can be modified within certain limits by purification in this way.

The following Examples are intended to illustrate the invention without limiting it in any way.

EXAMPLES

1. Starting materials

The diol mixture used for the cyclization in Example 1 was prepared in a 5-step synthesis sequence: to this end, nerolidol (isomer mixture) was convened by phosphorus tribromide in pyridine into farnesyl bromide (1) which was reacted with potassium cyanide to the corresponding nitrile (2). Saponification of the nitrile with potassium hydroxide gave homofarnesylic acid (3) which was cyclized with tin(IV) chloride to the lactone mixture (4). Finally, reduction of (4) with lithium aluminum hydride gave the did mixture (5). Steps (2) to (5) were carried out in accordance with Example 1 a-d) of DE 32 40 054 A1.

Acidic aluminum oxide

Commercial HCl-loaded aluminum oxide (a product of ICN Biomedicals). The pH value of a 5% by weight aqueous suspension was 4.5.

2. Analysis

The diol mixture (5) and the stereoisomer mixtures of $8\alpha,12$-oxido-13,14,15,16-tetranorlabdane obtained therefrom by cyclization are analytically characterized by coupling GC with MS. A 25 m quartz column (WG 11 ) 0.2 µm in diameter was used in the GC section. An ITD-Finnegan mass spectrometer was used for ion trap detection in the MS section. The detection limit of the method was 0.2%. Because a non-chiral column was used, all the data relate to racemic mixtures.

3. Production methods

3.1. Diol mixture (1) Farnesyl bromide:

203.2 g of nerolidol were initially introduced at −8° to −10° C. A mixture of 20.3 g of pyridine and 101.6 g of phosphorus tribromide was then added dropwise over a period of 4 hours (exothermic reaction). For working up, the solution was poured onto 400 ml of cold sodium carbonate solution and the mixture formed was extracted with diethyl ether. After drying with sodium sulfate, the combined organic phases were stored at −30° C. and were only concentrated at the lowest possible temperature immediately before further processing.

(2) Homofarnesylic acid nitrile:

262.1 g of farnesyl bromide, 91.2 g of potassium cyanide, 150 ml of water and 7.7 g of tetrabutyl ammonium chloride were initially introduced and the mixture was heated to 60° C. After the reaction had started, the temperature of the mixture was kept by cooling at 80° C. After the reaction had abated, the reaction mixture was stirred for another 2 hours at 60° C. For working up, the organic phase was separated off, washed twice with 200 ml of water, and dried over sodium sulfate. The product was distilled through a short Vigreux column. Yield: 108.7 g (52% of the theoretical over the first two stages). IR spectrum: i.a. band at 2200 cm$^{-1}$.

(3) Homofarnesylic acid:

108.7 g of the nitrile (2), 66.9 g of potassium hydroxide, 600 ml of ethanol, and 80 ml of water were initially introduced and the mixture was refluxed for 5 hours. The ethanol was then distilled off and the residue was dissolved in 2300 ml of water. The solution was extracted twice with 250 ml of ether. The organic phase was discarded. The aqueous phase was acidified with 700 ml of 20% sulfuric acid and then extracted three times with 250 ml of ether. The organic phases were combined, washed with water, dried over sodium sulfate, and concentrated. Yield: 97.5 g of a yellow oil (83% of the theoretical).

(4) Lactone mixture:

79.5 g of homofarnesylic acid were initially introduced into 480 ml of anhydrous methylene chloride and cooled to −78° C. 100 g of tin(IV) chloride were added dropwise over a period of 1 hour, followed by stirring for 2 hours at −78° C. For working up, the mixture was poured onto 600 ml of water and the organic phase was separated off. The organic solution was washed with saturated sodium carbonate solution and with water, dried over sodium sulfate, and the solvent was distilled off. The lactone mixture was obtained in a quantitative yield.

(5) Diol mixture:

79.5 g of the lactone mixture (4) were slowly added dropwise at room temperature to 24.1 g of lithium aluminum hydride in 200 ml of anhydrous diethyl ether (exothermic reaction). After complete addition, the mixture was stirred under reflux for another hour. For working up, the mixture was cooled and 100 ml of a 10% sodium hydroxide solution were added dropwise. The organic phase was then separated off and the aqueous phase was extracted with diethyl ether. The combined organic phases were washed with 10% sodium sulfate solution until neutral, dried over sodium sulfate, and concentrated. Yield: 75.9 g diol (94% of the theoretical). According to GC/MS analysis, the diol mixture obtained contained:

| | |
|---|---|
| Diol intermediate of 8a,12-oxido-13,14,15,16-tetranorlabdane | 31.2% |
| Diol intermediate of the 9-epi isomer of 8a,12-oxido-13,14,15,16-tetranorlabdane | 19.8% |
| Diol intermediate of the 8-epi isomer of 8a,12-oxido-13,14,15,16-tetranorlabdane | 2.0% |
| | 53.0% |

3.2. Example 1: $8\alpha,12$-oxido-13,14,15,16-tetranorlabdane mixture 130 g of the diol mixture (5) were dissolved in 200 ml of toluene. 102 g of acidic aluminum oxide were added to the solution which was then heated with stirring to the boiling temperature. Water was separated at the water separator. After 1 hour, the separation of water stopped and the temperature was adjusted to 150° C. by removal of toluene from the water separator. At the same time, more water was continuously removed from the circuit. When the separation of the water stopped (after about 4 hours), the hot reaction mixture was filtered off from the aluminum oxide and was then rinsed with 50 ml of hot toluene. 123 g of crude product were obtained. Analysis of the product by GC/MS showed that it contained:

| | |
|---|---|
| AMBROXAN ® | 30.8% |
| 9-epi Isomer of 8a,12-oxido-13,14,15,16-tetranorlabdane | 19.4% |
| 8-epi Isomer of 8a,12-oxido-13,14,15,16-tetranorlabdane | 2.0% |
| | 52.2% |

The cyclization yield is thus 98.:5% of the theoretical.

The invention claimed is:

1. A process for the production of stereoisomer mixtures of 8,12-oxido-13, 14,15,16-tetranorlabdane by cyclizing dehydration of stereoisomer mixtures of 8,12-dihydroxy-13,14,15,16-tetranorlabdane, wherein acid-loaded aluminum oxide is used for the cyclization.

2. A process as claimed in claim 1, wherein the cyclization is carried out at temperatures of 140° to 160° C.

3. A process as claimed in claim 2, wherein the cyclization is carried out in an inert solvent.

4. A process as claimed in claim 3, wherein the acid-loaded aluminum oxide is used in a quantity of 60 to 80% by weight, based on the 8,12-dihydroxy- 13,14,15,16-tetranorlabdane.

5. A process as claimed in claim 1, wherein the cyclization is carried out at temperatures of 120° to 180 ° C.

6. A process as claimed in claim 5, wherein the cyclization is carried out in an inert solvent.

7. A process as claimed in claim 1, wherein the cyclization is carried out in an inert solvent.

8. A process as claimed in claim 7, wherein the acid-loaded aluminum oxide is used in a quantity of 40 to 100% by weight, based on the 8,12-dihydroxy-13,14,15,16-tetranorlabdane.

9. A process as claimed in claim 8, wherein the acid-loaded aluminum oxide is used in a quantity of 60 to 80% by weight, based on the 8,12-dihydroxy-13,14,15,16-tetranorlabdane.

10. A process as claimed in claim 6, wherein the acid-loaded aluminum oxide is used in a quantity of 40 to 100% by weight, based on the 8,12-dihydroxy-13,14,15,16-tetranorlabdane.

11. A process as claimed in claim 10, wherein the acid-loaded aluminum oxide is used in a quantity of 60 to 80% by weight, based on the 8,12-dihydroxy-13,14,15,16-tetranorlabdane.

12. A process as claimed in claim 5, wherein the acid-loaded aluminum oxide is used in a quantity of 40 to 100% by weight, based on the 8,12-dihydroxy-13,14,15,16-tetranorlabdane.

13. A process as claimed in claim 12, wherein the acid-loaded aluminum oxide is used in a quantity of 60 to 80% by weight, based on the 8,12-dihydroxy-13,14,15,16-tetranorlabdane.

14. A process as claimed in claim 2, wherein the acid-loaded aluminum oxide is used in a quantity of 40 to 100% by weight, based on the 8,12-dihydroxy-13,14,15,16-tetranorlabdane.

15. A process as claimed in claim 14, wherein the acid-loaded aluminum oxide is used in a quantity of 60 to 80% by weight, based on the 8,12-dihydroxy-13,14,15,16-tetranorlabdane.

16. A process as claimed in claim 1, wherein the acid-loaded aluminum oxide is used in a quantity of 40 to 100% by weight, based on the 8,12-dihydroxy-13,14,15,16-tetranorlabdane.

17. A process as claimed in claim 16, wherein the acid-loaded aluminum oxide is used in a quantity of 60 to 80% by weight, based on the 8,12-dihydroxy-13,14,15,16-tetranorlabdane.

18. The process of claim 1 wherein the stereoisomer mixtures of 8,12-oxido- 13,14,15,16-tetranorlabdane comprise $8\alpha,12$-oxido-13,14,15,16-tetranorlabdane, and the 9-epi isomer and the 8-epi isomer of the foregoing.

19. The process of claim 18 wherein the cyclization is carried out at a temperature in the range of 120° to 180° C.

* * * * *